United States Patent
Noveron et al.

(10) Patent No.: US 9,987,363 B2
(45) Date of Patent: Jun. 5, 2018

(54) MATERIALS WITH WATER-TRIGGERED DRUG-RELEASE PROPERTIES FOR LOCALIZED THERAPEUTICS

(71) Applicants: Juan Noveron, El Paso, TX (US); Shokooh Bahadorzadeh, El Paso, TX (US)

(72) Inventors: Juan Noveron, El Paso, TX (US); Shokooh Bahadorzadeh, El Paso, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days. days.

(21) Appl. No.: 15/408,014

(22) Filed: Jan. 17, 2017

(65) Prior Publication Data
US 2017/0209382 A1 Jul. 27, 2017

Related U.S. Application Data

(60) Provisional application No. 62/279,223, filed on Jan. 15, 2016.

(51) Int. Cl.
*A61K 47/32* (2006.01)
*A61K 9/06* (2006.01)

(52) U.S. Cl.
CPC ............... *A61K 47/32* (2013.01); *A61K 9/06* (2013.01)

(58) Field of Classification Search
CPC .................................. A61K 47/32; A61K 9/06
See application file for complete search history.

(56) References Cited

PUBLICATIONS

Ettmayer et al., "Lessons learned from marketed and investigational prodrugs." J. Med. Chem. 47(10), 2004, pp. 2393-2404.
Ganta et al., "A review of stimuli-responsive nanocarriers for drug and gene delivery." J. Control. Release, 126, 2008, pp. 187-204.
Kidane et al., "Recent advances in small molecule drug delivery." Curr. Opin. Chem. Biol., 9, 2005, pp. 347-351.

*Primary Examiner* — Trevor Love
(74) *Attorney, Agent, or Firm* — Norton Rose Fulbright US LLP (57) ABSTRACT

Methods, devices, and/or systems for providing a three-dimensional printing of a structure encapsulating a drug comprising at least one Zn(II) complexed with acrylate groups capable of forming a 3D structure and capable of encapsulating a drug.

15 Claims, 3 Drawing Sheets

MATERIALS WITH WATER-TRIGGERED DRUG-RELEASE PROPERTIES FOR LOCALIZED THERAPEUTICS

PRIORITY PARAGRAPH

This Application claims priority to U.S. Provisional Patent Application Ser. No. 62/279,223 filed Jan. 15, 2016, which is incorporated herein by reference in its entirety.

BACKGROUND

Embodiments described herein are related to the field of drug delivery compositions and to the uses thereof, especially in medicine and health care and in particular localized medical delivery of drugs.

A large number of pharmaceutically active compounds have not achieved clinical applications due to poor bioavailability (Kidane and Bhatt, 2005 Curr. Opin. Chem. Biol., 9: 347-51). The route of clinical administration plays a big role in the physiological and metabolic properties of the drugs, and when systemic distribution is used, it often triggers side effects that outweigh the therapeutic benefits of treatment (Wang et al. Drug delivery: principles and applications. John Wiley and Sons, NJ (2005)). Localized therapeutics with controlled released provide an alternative route in regulating the bioavailability of the pharmaceutical agents. This can lead to therapies with decreased side effects and lower minimum effective dose required for clinical results.

Nanocarriers for drug delivery are nanomaterials used as a transport means for a drug. Nanocarriers possess unique characteristics that show potential for use in drug delivery. Although many nanocarriers have been reported before (Ganta et al. 2008 J. Control. Release, 126: 187-204), there is a continuing need for nanocarriers that deliver drugs more effectively, are easy to produce, and deliver drugs with appropriate dosages upon appropriate stimuli.

Three dimensional (3D) printing has shown promise as a means to prepare drug delivery systems that improve the timing of delivery, dose of the drug, location of delivery, cost of manufacture, etc. 3D printing also provides the ability to create custom delivery systems tailored for the individual patient. However, a major limitation to the use of 3D printing for drug delivery systems is the limited number of materials that are both biocompatible and capable of being used as an ink and/or filament in 3D printing. Further, the conditions required to produce an ink and/or filament that flows sufficiently for 3D printing and the conditions for curing the ink/filament once printed can also limit the compatibility of 3D printing with a drug of choice.

Thus, there is a need for additional 3D printing solutions that are compatible with a large range of drug delivery systems and drugs.

SUMMARY

Embodiments are directed to drug delivery compositions that are 3D printable as a gel with stimuli-responsive delivery properties that release pharmaceuticals upon exposure to traces of water molecules. In certain aspects the drug delivery composition as described herein comprises Zn(II) acrylate complexes. As further disclosed herein, the technology can be applied in many fields. In particular the technology can be applied to the medical field and to the drug delivery field. In some embodiments of the invention as disclosed herein, drug delivery technologies can include, but are not limited to, localized drug delivery.

Certain embodiments are directed to compounds, materials, and/or devices comprising a Zn(II) acrylate complex having general Formula I:

Formula I wherein X is oxygen (O), nitrogen (N), or sulfur (S), and $R_1$ is benzamide. In certain aspects X is N and $R_1$ is benzamide.

Certain embodiments are directed to an encapsulated drug composition comprising a selected drug encapsulated by a gel formed by Zn(II) acrylate complexes having a structure of Formula I. In certain aspects X is nitrogen (N), oxygen (O), or sulfur; and $R_1$ is benzamide. Release of the selected drug is triggered by contacting the gel with a sufficient amount of water. In certain aspects the selected drug is a prodrug. The composition can further comprise at least 1, 2, 3, 4, 5 or more drugs or excipients. In certain aspects all or portions of the gel are UV crosslinked.

A further embodiment is directed to a substrate, ink or filament, for a three dimensional printer comprising a print material comprising complexes of Formula I.

Certain embodiments are directed to a Zn(II) acrylate encapsulation device comprising: an exterior, water triggered gel comprising a Zn(II) acrylate complex of Formula I; and at least one drug encapsulated by the exterior gel. The device can be in the form of a patch, cylinder, sphere, or any other three dimensional polygonal that can form a cavity for encapsulating a drug. In certain aspects the drug is a prodrug. In a further aspect the drug or prodrug is an anti-proliferative drug, an anti-cancer drug, an anti-microbial drug, or an anti-inflammatory drug. In certain aspects the Zn(II) acrylate complex is Zn(II) acrylate bis(N-pyridyl benzamide).

Still other embodiments are directed to methods for delivering a drug (or prodrug) to a predetermined location in a subject comprising positioning an encapsulation device or composition as described herein at a predetermined location in or on a subject in need thereof. In certain aspects the device or composition is surgically implanted in a subject. In other aspects the device or composition is placed on an external surface of a subject. The external surface of the subject can be the epidermis or a mucosal membrane of the subject.

Certain embodiments are directed to methods of making a Zn(II) acrylate complex print material or Zn(II) acrylate complex gels. A Zn(II) acrylate complex print material can be made by dissolving Zn(II) acrylate and a complexing reagent (e.g., N-phenyl-benzamide (NPBA)) in an appropriate solvent. The solution can be concentrated, using for example rotary evaporation. A crystallization catalyst can be added (e.g., diethyl ether) and the concentrated solution left to form crystals of the Zn(II) acrylate complex product (e.g., Zn(II) acrylate bis(N-pyridyl benzamide)). The product can be further processed to form an ink or filament composition.

A Zn(II) acrylate complex gel can be made by assembling a plurality of Zn(II) acrylate complexes to form an at least two layer gel encapsulating a drug between the at least two layers of gel. In certain aspect each layer is UV crosslinked or cured, but not necessarily at the same time. In certain aspects the assembly of the plurality of Zn(II) acrylate complexes is by stereolithography. In a further aspect the Zn(II) acrylate complex is Zinc(II) acrylate bis(N-pyridyl benzamide).

"Prodrug" refers to a derivative of an active drug that requires a transformation under the conditions of use, such as within the body, to release the active drug. Prodrugs are frequently, but not necessarily, pharmacologically inactive until converted into the active drug. Prodrugs are typically obtained by masking one or more functional groups in an active drug believed to be in part required for activity with a progroup to form a promoiety which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid or base, or by a change of or exposure to a physical or environmental parameter, such as a change of temperature. The agent may be endogenous to the conditions of use, such as an enzyme present in cells, tissue, organ, or location to which the prodrug is administered.

"Progroup" refers to a type of protecting group that, when used to mask a functional group within an active drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH$_3$ comprises the progroup —C(O)CH$_3$.

A "therapeutically effective amount" means an amount capable of invoking one or more of the following effects: (1) inhibition, to some extent, of disease or condition, including slowing progression or complete arrest; (2) reducing the number of pathologic cells; (3) reduction in lesion size; (4) inhibition (i.e., reduction, slowing down, or complete stopping) of pathologic cell infiltration into peripheral organs; (5) inhibition (i.e., reduction, slowing down, or complete stopping) of the disease or condition; (6) enhancement of therapeutic response, which may, but is not required to, result in the regression of a disease or condition, or (7) relief, to some extent, of one or more symptoms associated with the disease or condition. The therapeutically effective amount may vary according to factors such as the disease state, age, sex and weight of the individual and the ability of one or more therapeutic agents to elicit a desired response in the individual. A "therapeutically effective amount" is also one in which any toxic or detrimental effects are outweighed by the therapeutically beneficial effects.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain') are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 1 3-D printable materials (capsules or patches) with water-triggered drug-release properties.

DESCRIPTION

Embodiments are directed to a drug delivery composition that is 3-D printable having a stimuli-responsive delivery properties that release pharmaceuticals upon exposure to traces of water molecules. In certain aspect the 3D material is in the form of a gel. In certain aspect the gel comprises a Zn(II) acrylate complex. The broad family of Zn(II) complexes comprising acrylate groups, as exemplified in the non-limiting example of Zinc(II) acrylate bis(N-pyridyl benzamide).

The compositions described herein may be applied in treating any organism. In certain aspects the organism is a mammal, such as humans, pets, or livestock. In particular, the human body contains between 50-70% water, depending on the age and gender; thus, water-triggered release of pharmaceuticals has potential applications in localized therapies such as in anti-cancer treatment, infectious diseases, and surgery.

The capacity to release a drug when exposed to a trigger, such as water (water trigger) may be determined by means known in the art. In a non-limiting example, a water trigger release may be determined by monitoring for the loss of drug from a composition or the increased presence of drug in solution before, during, and/or after contact with water. A non-limiting means of monitoring for the loss of a drug after addition is monitoring the change in absorbance of a 3D printed structure or a solution in which the structure is immersed. The particular wavelength of interest can be determined by the characteristic of the moiety to be monitored.

Further, in some embodiments, printed structures containing Zn(II) acrylate complexes can be obtained or produced at a reduced cost compared to other 3D printed structure with a drug encapsulated therein.

Compositions and components described herein can be used or applied in many different medical applications. As a non-limiting example, some embodiments of the invention compositions can be used in colonoscopy for the in situ treatment of pre-cancerous polyps in which over 14 million Americans get screened every year. Another non-limiting example includes application in the treatment of gallbladder infections that require localizing high concentrations of antibiotics to avoid amputation of the gallbladder.

Figure 1:
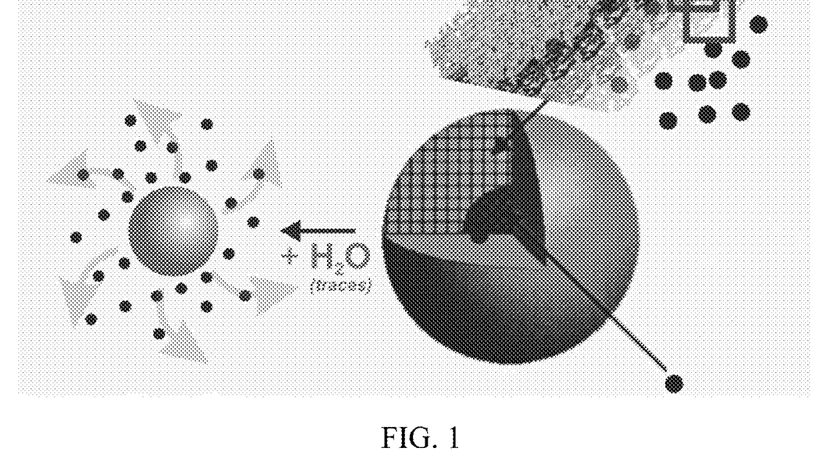
Figure 2:
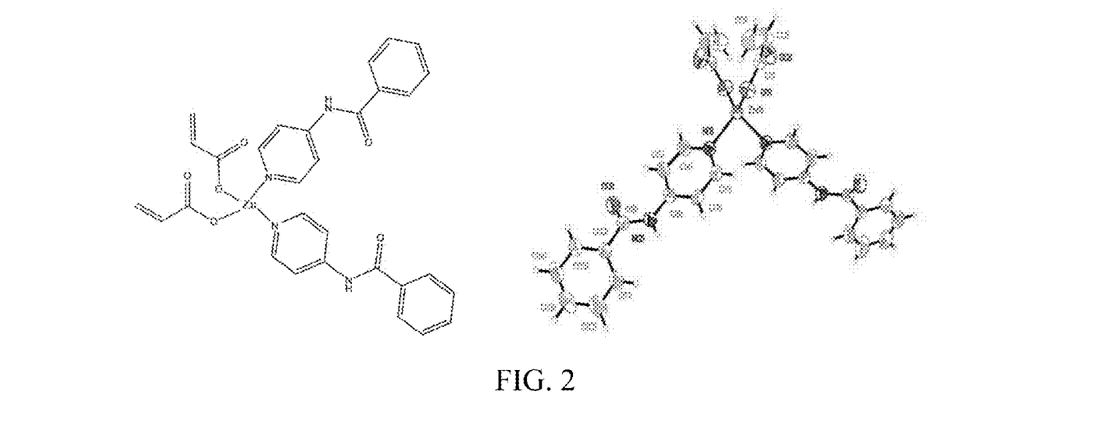
FIG. 2 Molecular structure of a preferred embodiment of the present invention, Zinc(II) acrylate bis(N-pyridyl benzamide).

FIG. 1 provides a non-limiting example of this approach using 3-D printable materials (capsules or patches) with water-triggered drug-release properties.

I. Production of Zn(II) Acrylate Gels

Zn(II) acrylate complexes can be assembled and/or polymerized into a drug encapsulation device using 3D-printing technologies. The Zn(II) acrylate encapsulation devices provide a delivery system that is better suited for localized delivery a drug. For example, the rate of delivery can be modulated based on the designed surface area of a Zn(II) acrylate encapsulation device providing for delivery of a drug to a localized area of a subject at a predetermined rate.

In certain embodiments three dimensional drug delivery objects are produced using stereolithography. Stereolithography is an additive manufacturing process that works by focusing an ultraviolet (UV) laser on a photopolymer resin. With the help of computer aided manufacturing or computer aided design software (CAM/CAD), the UV laser is used to draw a pre-programmed design or shape on to the surface of the photopolymer. Because photopolymers are photosensitive under ultraviolet light, the resin is solidified and forms a single layer of the desired 3D object. This process is repeated for each layer of the design under the 3D object is complete.

In certain aspects an elevator apparatus can be used, where an elevator platform descends a distance equal to the thickness of a single layer of the design (typically 0.05 mm to 0.15 mm into the photopolymer, followed by sweeping with a resin-filled blade re-coating it with fresh photopolymer material. The subsequent layer is traced, joining the previous layer. A complete 3D object can be formed using this process. Designs are typically then immersed in a chemical bath in order to remove any excess resin and cured in an ultraviolet oven.

In certain aspects stereolithography uses supporting structures that attach to a movable platform that holds cross sections in place in order to resist lateral pressure from the resin-filled blade. Supports are created automatically during the preparation of 3D Computer Aided Design models and can also be made manually.

3D printing may be performed by many different methods. In some embodiments, the 3-D printing method may be accomplished by deposition of Zn(II) acrylate complex by an array of nozzles. In some embodiments, the deposition may deposit in small, precise portions, such as in micrometer sized portions or smaller. In some embodiments, the materials may be deposited in liquid, powder, sheet or other forms. In some embodiments, there is a separate array of nozzles for at least one portion of each layer and/or more than one material may be printed at the same time or different times. In some embodiments, different materials may be deposited on the same layer simultaneously (either as a mixture or by separate nozzles) or sequentially.

In some embodiments, portions of a layer previously deposited may be removed prior to or after subsequent depositions. Layers may be removed by techniques known in the art, such as etching, lasers, engraving, or peeling. In some embodiments, removing portions of a layer previously deposited may be used to create pores or additional surface area on the invention as described herein. In some embodiments, removing portions of a layer previously deposited may be used to deposit different materials within the areas that were removed, such as depositing drug or drug containing material in the portions that were previously removed.

The 3D printing is not limited to any specific 3-D printing machine, software, or 3D shape.

Prodrugs are derivatives of drug compounds that require transformation under the conditions of use, such as within the body, to release the active drug. Prodrugs are frequently, but not necessarily, pharmacologically inactive until converted into the active drug. Prodrugs are typically obtained by masking a functional group in the drug believed to be in part required for activity with a progroup to form a promoiety which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid, or by a change of or exposure to a physical or environmental parameter, such as a change of temperature. The agent may be endogenous to the conditions of use an enzyme present in the location to which the prodrug is administered, the conditions of the location such as the acidity of the stomach and the like, or it may be supplied exogenously.

Prodrug compounds useful in the methods described herein are generally compounds that when administered in an amount effective to, and under conditions suitable to, yield an amount of a drug that is therapeutically effective.

A progroup can include, but is not limited to, a group or moiety that is metabolized under the conditions of use to yield a therapeutic or active agent. In some embodiments, the progroup may be, but is not limited to, an acid labile hydroxyalkyl-containing progroup, an acid labile thio containing progroup, an acid labile amino containing progroup, an acid labile phosphate containing progroup, and salts thereof. Each of the acid labile thio containing progroup and the acid labile amino containing progroup may be thioalkyl and aminoalkyl groups, respectively. In some embodiments the acid labile hydroxyalkyl-containing progroup, acid labile thio containing progroup, and an acid labile amino containing progroup may be capped as the corresponding phosphate, e.g., —$CH_2$—O—P(O)(OH)$_2$, thiophosphate, e.g. —$CH_2$—S—P(O)(OH)$_2$, and phosphoramidate, e.g. —$CH_2$—NH—P(O)(OH)$_2$, respectively, to make prodrug groups. These prodrug groups can be free acids as depicted, alkyl esters, or salts, e.g. metal salts, and combinations thereof.

The mechanism by which the progroup is cleaved or metabolized is not critical, and can be caused by, for example, hydrolysis under the acidic conditions, and/or by enzymes present in the fluids, tissues, or organs of the body. Indeed, the progroup(s) can be selected to metabolize at a particular site within the body. For example, many esters are cleaved under the acidic conditions found in the stomach. Alternatively, the progroups may be designed to cleave or metabolize in the presence of enzymes such as esterases, amidases, lipolases, phosphatases including ATPases and kinase etc. Progroups including linkages capable of metabolizing in vivo to yield an active compound are well-known, and include, by way of example and not limitation, ethers, thioethers, silylethers, silylthioethers, esters, thioesters, carbonates, thiocarbonates, carbamates, thiocarbamates, ureas, thioureas, carboxamides, etc. In some instances, a "precursor" group that is oxidized by oxidative enzymes such as, for example, cytochrome P450 of the liver, to a metabolizable group, can be selected.

The identity of the progroup can also be selected so as to impart the prodrug with desirable characteristics. For example, lipophilic groups can be used to decrease water solubility and hydrophilic groups can be used to increase water solubility. In this way, prodrugs specifically tailored for selected modes of administration can be obtained. The progroup can also be designed to impart the prodrug with other properties, such as, for example, improved passive intestinal absorption, improved transport-mediated intestinal absorption, protection against fast metabolism (slow-release prodrugs), tissue-selective delivery, passive enrichment in target tissues, targeting-specific transporters, etc. Groups capable of imparting prodrugs with these characteristics are well-known, and are described, for example, in Ettmayer et al., 2004, *J. Med. Chem.* 47(10: 2393-2404).

II. Pharmaceutical Formulations

In certain embodiments, the invention also provides compositions comprising 1, 2, 3 or more drugs or therapeutic agents with one or more of the following: a pharmaceutically acceptable diluent; a carrier; a solubilizer; an emulsifier; a preservative; and/or an adjuvant. Such compositions may contain an effective amount of at least one active agent or a prodrug thereof.

The active agents may be formulated into therapeutic compositions in a variety of dosage forms such as, but not limited to, liquid solutions, suspensions, or powders that can be encapsulated in the compositions and devices described herein. The preferred form depends upon the mode of administration and the particular disease targeted. The compositions also preferably include pharmaceutically acceptable vehicles, carriers, or adjuvants, well known in the art.

Acceptable formulation components for pharmaceutical preparations are nontoxic to recipients at the dosages and concentrations employed. In addition to the active agents that are provided, compositions may contain components for modifying, maintaining, or preserving, for example, the pH, osmolarity, viscosity, clarity, color, isotonicity, odor, sterility, stability, rate of dissolution or release, adsorption, or penetration of the active agent. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (see *Remington's Pharmaceutical Sciences*, 18 th Ed., (A. R. Gennaro, ed.), 1990, Mack Publishing Company), hereby incorporated by reference.

Formulation components are present in concentrations that are acceptable to the site of administration. Buffers are advantageously used to maintain the composition at physiological pH or at a slightly lower pH, typically within a pH range of from about 4.0 to about 8.5, or alternatively, between about 5.0 to 8.0. Pharmaceutical compositions can comprise TRIS buffer of about pH 6.5-8.5, or acetate buffer of about pH 4.0-5.5, which may further include sorbitol or a suitable substitute therefor.

The pharmaceutical composition to be used for in vivo administration is typically sterile. Sterilization may be accomplished by filtration through sterile filtration membranes. If the composition is lyophilized, sterilization may be conducted either prior to or following lyophilization and reconstitution.

Once the pharmaceutical composition of the invention has been formulated, it may be incorporated into the water triggered gel described herein. Such compositions or devices may be stored either in a ready-to-use.

The active agents or drugs of the present invention, alone or as part of a pharmaceutical composition, can be provided at doses between about 0.001 mg/kg and 1 mg/kg body weight, preferably between about 1 and 100 μg/kg body weight, most preferably between 1 and 10 μg/kg body weight. Therapeutically effective doses will be easily determined by one of skill in the art and will depend on the severity and course of the disease, the patient's health and response to treatment, the patient's age, weight, height, sex, previous medical history and the judgment of the treating physician.

Some methods may further involve performing surgery on the patient, such as by resecting all or part of a tissue or organ. Compositions or devices described herein may be administered to the patient before, after, or at the same time as surgery. In additional embodiments, compositions or devices may be administered directly, endoscopically, intratracheally, intratumorally, intravenously, intralesionally, intramuscularly, intraperitoneally, regionally, percutaneously, topically, intrarterially, intravesically, or subcutaneously.

III. Examples

Example 1

3D Printing

Figure 4:
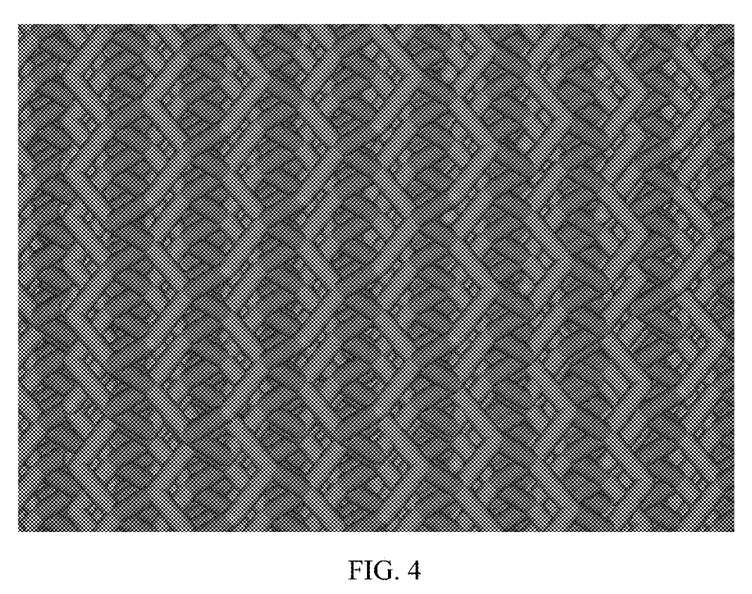
FIG. 4 A non-limiting example of 3-D structures printed with an embodiment of the gels disclosed herein.
Figure 5:
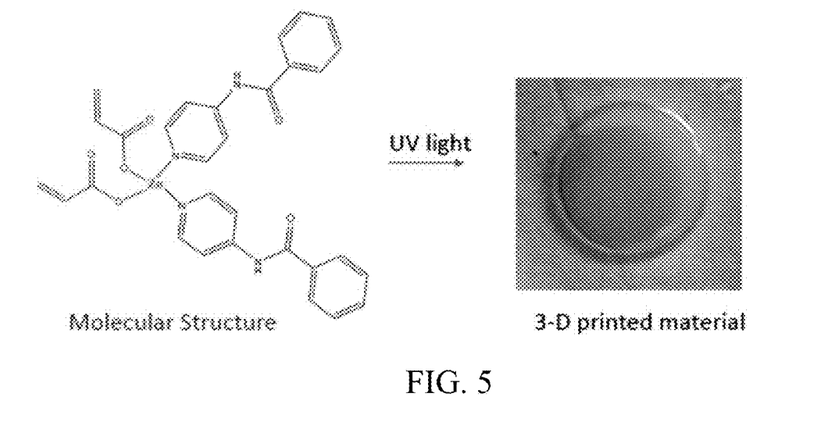
FIG. 5 Photograph of an embodiment of the 3-D printed material disclosed herein after exposure to UV light.

Encapsulating pharmaceuticals or drugs in a Zn(II) acrylate complex gel is exemplified by using Zn(II) acrylate bis(N-pyridyl benzamide). Zn(II) acrylate bis(N-pyridyl benzamide) was used as a liquid solution ink wherein each layer was cured using UV light before the next layer was applied (FIG. 5). Zn(II) acrylate bis(N-pyridyl benzamide) is compatible with 3D printing of microstructures, such as the high-surface area material show in FIG. 4. Further, 3D printing of some of the embodiments disclosed herein allows for the formation of patches for localized therapeutics.

Example 2

Water-Triggered Release of Encapsulated Pharmaceuticals

Figure 3:
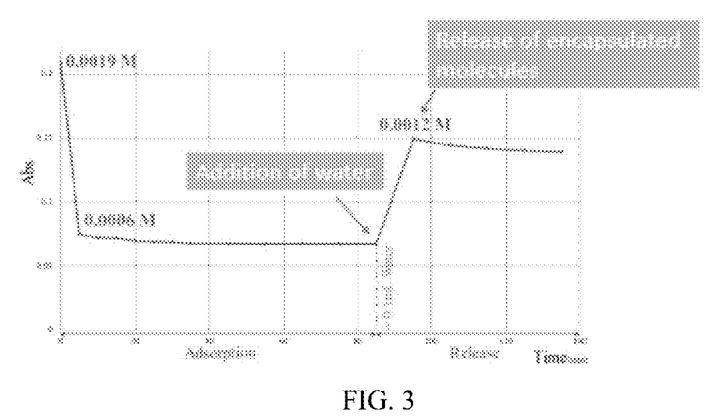
FIG. 3 Water-triggered release properties followed with UV-vis spectroscopy.

Water-triggered release of encapsulated pharmaceuticals was demonstrated for a representative example of a Zn(II) acrylate complex, Zn(II) acrylate bis(N-pyridyl benzamide). UV-vis spectroscopy was used to determine the release of a pharmaceutical or drug encapsulated in an anhydrous suspension of a 3D printed Zn(II) acrylate bis(N-pyridyl benzamide) gel using a trace amount of water as a trigger. It was demonstrated that the addition of 0.1 ml of water to the anhydrous suspension caused a rapid release of the pharmaceutical (FIG. 3) from the Zn(II) acrylate bis(N-pyridyl benzamide) gel into the solution as determined by the increase in absorbance of the solution of a wavelength absorbed by the pharmaceutical.

The invention claimed is:

1. An encapsulated drug composition comprising a selected drug encapsulated by a gel formed by complexes having a structure of Formula I Formula I wherein X is nitrogen (N), oxygen (O), or sulfur; and $R_1$ is benzamide, wherein release of the selected drug is triggered by contact with a sufficient amount of water.

2. The composition of claim 1, wherein the selected drug is a prodrug.

3. The composition of claim 1, further comprising at least a second selected drug.

4. The composition of claim 1, wherein the compound of Formula I is crosslinked by exposure to UV light.

5. A substrate for a three dimensional printer comprising a print material comprising a compound having a structure of Formula I Formula I wherein X is nitrogen (N), oxygen (O), or sulfur; and $R_1$ is benzamide, wherein the material is in the form of a three dimensional printer filament.

6. A Zn(II) acrylate encapsulation device composition comprising an exterior, water triggered gel comprising a Zn(II) acrylate complex of Formula I Formula I wherein X is nitrogen (N), oxygen (O), or sulfur; and $R_1$ is benzamide;
and at least one drug encapsulated by the exterior gel.

7. The device of claim 6, wherein the drug is a prodrug.

8. The device of claim 6, wherein the drug is an antiproliferative drug.

9. The device of claim 6, wherein the drug is an anticancer drug.

10. The device of claim 6, wherein the gel is UV crosslinked.

11. The composition of claim 6, wherein the Zn(II) complex is Zinc(II) acrylate bis(N-pyridyl benzamide).

12. A method for delivering a drug to a predetermined location in a subject comprising positioning the device of claim 6 at a predetermined location in or on a subject in need thereof.

13. The method of claim 12, wherein the device is surgically implanted in a subject.

14. The method of claim 12, wherein the device is on an external surface of a subject.

15. The method of claim 14, wherein the external surface of the subject is epidermis or mucosal membrane of the subject.

* * * * *

UNITED STATES PATENT AND TRADEMARK OFFICE
CERTIFICATE OF CORRECTION

| | |
|---|---|
| PATENT NO. | : 9,987,363 B2 |
| APPLICATION NO. | : 15/408014 |
| DATED | : June 5, 2018 |
| INVENTOR(S) | : Juan C. Noveron and Shokooh Bahadorzadeh |

Page 1 of 1

It is certified that error appears in the above-identified patent and that said Letters Patent is hereby corrected as shown below:

In the Specification

Please add the following at Column 1, before Line 11:
STATEMENT REGARDING FEDERALLY FUNDED RESEARCH
This invention was made with government support under DMR1205302 awarded by the National Science Foundation. The government has certain rights in the invention.

Signed and Sealed this
Twenty-eighth Day of January, 2025

Coke Morgan Stewart
*Acting Director of the United States Patent and Trademark Office*